(12) United States Patent
Saini et al.

(10) Patent No.: US 7,740,801 B2
(45) Date of Patent: Jun. 22, 2010

(54) SYSTEM FOR DETERMINATION OF AN ANALYTE IN A BODILY FLUID SAMPLE THAT INCLUDES AN ELECTROLUMINESCENT COMPONENT

(75) Inventors: Selwayan Saini, Culbokis (GB); Marco Fabio Cardosi, Croy (GB); Leanne Mills, Inverness (GB); Stephen Patrick Blythe, Inverness (GB)

(73) Assignee: LifeScan Scotland Limited, Scotland (GB)

( * ) Notice: Subject to any disclaimer, the term of this patent is extended or adjusted under 35 U.S.C. 154(b) by 429 days.

(21) Appl. No.: 11/591,138

(22) Filed: Oct. 31, 2006

(65) Prior Publication Data
US 2008/0101985 A1     May 1, 2008

(51) Int. Cl.
    *G01N 21/76* (2006.01)
(52) U.S. Cl. .......................................... 422/52
(58) Field of Classification Search .............. 422/52
    See application file for complete search history.

(56) References Cited

U.S. PATENT DOCUMENTS

| | | | |
|---|---|---|---|
| 3,052,810 A | | 9/1962 | Mash |
| H000044 H | * | 4/1986 | Moran ........................ 327/240 |
| 4,935,346 A | * | 6/1990 | Phillips et al. ................ 435/14 |
| 5,426,032 A | | 6/1995 | Phillips et al. |
| 5,453,359 A | * | 9/1995 | Gargan et al. ................. 435/13 |
| 5,453,360 A | | 9/1995 | Yu et al. |
| 5,675,217 A | | 10/1997 | Kang |
| 5,753,452 A | | 5/1998 | Smith |
| 6,168,957 B1 | | 1/2001 | Matzinger et al. |
| 6,514,460 B1 | | 2/2003 | Fendrock |
| 6,555,061 B1 | * | 4/2003 | Leong et al. .................. 422/58 |
| 6,743,164 B2 | * | 6/2004 | Airaudi et al. ................ 600/27 |
| 6,800,722 B2 | | 10/2004 | Pei |
| 6,821,482 B1 | | 11/2004 | Albert et al. |
| 2003/0218420 A1 | | 11/2003 | Zovko |
| 2005/0023137 A1 | | 2/2005 | Bhullar et al. |
| 2005/0023972 A1 | | 2/2005 | Lewandowski et al. |

FOREIGN PATENT DOCUMENTS

| | | |
|---|---|---|
| EP | 1288653 A1 * | 3/2003 |
| EP | 1672356 A1 | 6/2006 |
| GB | 2 431 231 A | 4/2007 |
| WO | WO 9417556 A1 * | 8/1994 |
| WO | WO 01/38857 A1 | 5/2001 |

(Continued)

OTHER PUBLICATIONS

Mao, H.; Yang, T.; Cremer, P.S. "Design and Characterization of Immobilized Enzymes in Microfluidic Systems" Analytical Chemistry, 2002, 74 (2), pp. 379-385.*

(Continued)

*Primary Examiner*—Walter D Griffin
*Assistant Examiner*—Bobby Ramdhanie

(57) ABSTRACT

A system for the determination of an analyte in a bodily fluid sample includes an analytical test strip and an analytical meter. The analytical test strip has a substrate layer, an electroluminescent component (either an electroluminescent module and/or an electroluminescent lamp) disposed on the substrate layer, and a sample chamber configured for receiving a bodily fluid sample disposed above the substrate layer. Moreover, the analytical meter is configured for insertion of the analytical test strip therein and subsequent determination of the analyte.

11 Claims, 7 Drawing Sheets

FOREIGN PATENT DOCUMENTS

WO  WO 2005/078438 A2  8/2005
WO  WO 2005/103652 A1  11/2005

OTHER PUBLICATIONS

Zhou, Mingjie, et al., "A Stable Nonfluorescent Derivative of Resorufin for the Fluorometric Determination of Trace Hydrogen Peroxide: Applications in Detecting the Activity of Phagocyte NADPH Oxidase and Other Oxidases", Analytical Biochemistry, vol. 253, No. 2, Nov. 15, 1997, pp. 162-168.

Savvate'Ev, V., et al., "Integrated Organic Light-Emitting Device/ Fluorescence-Based Chemical Sensors", Applied Physics Letters, vol. 81, No. 24, Dec. 9, 2002, pp. 4652-4654.

* cited by examiner

SYSTEM FOR DETERMINATION OF AN ANALYTE IN A BODILY FLUID SAMPLE THAT INCLUDES AN ELECTROLUMINESCENT COMPONENT

The present invention is related to the following co-pending US applications: U.S. patent application Ser. No. 11/591,313, filed on Oct. 31, 2006, now abandoned; U.S. patent application Ser. No. 11/591,367, filed on Oct. 31, 2006; U.S. patent application Ser. No. 11/591,316, filed on Oct. 31, 2006, now abandoned; and U.S. patent application Ser. No. 11/591,366, filed on Oct. 31, 2006, now abandoned.

BACKGROUND OF THE INVENTION

1. Field of the Invention

The present invention relates, in general, to analytical devices and, in particular, to analytical test strips and related systems and methods.

2. Description of the Related Art

The determination (e.g., detection and/or concentration measurement) of an analyte (such as glucose) in a bodily fluid sample is of particular interest in the medical field. For example, it can be desirable to determine glucose, cholesterol, acetaminophen and/or HbA1c concentrations in a sample of a bodily fluid such as urine, blood or interstitial fluid. Such determinations can be achieved using analytical test strips based on, for example, photometric or electrochemical techniques, along with an associated meter.

Typical photometric analytical test strips employ a fluid sample application zone (e.g., a sample chamber), a photometric enzymatic reagent that engages in a photometric reaction (for example a color-inducing reaction) with an analyte of interest, and a detector of an associated meter to determine the concentration of the analyte. For example, a photometric analytical test strip for the determination of glucose concentration in a blood sample can employ a * photometric enzymatic reagent that includes the enzyme glucose oxidase and a chromophore (such as 3-methyl-2-benzothiazolinone hydrazone hydrocholoride [MBTH] and 3-dimethyaminobenzoic acid [DMAB]). Further details of conventional photometric analytical test strips are included in U.S. Pat. Nos. 5,753,452, 6,168,957, 6,555,061, 5,426,032 and 6,821,482, each of which is hereby incorporated in full by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings, of which.

DETAILED DESCRIPTION OF EXEMPLARY EMBODIMENTS OF THE INVENTION

An analytical test strip for the determination of an analyte (such as glucose) in a bodily fluid sample (e.g., a whole blood sample) according to various embodiments of the present invention includes a substrate layer, an electroluminescent module disposed on the substrate layer, a sample chamber (such as a capillary sample chamber) configured for receiving the bodily fluid sample disposed above the substrate layer and a fluorophore-containing photometric enzymatic reagent disposed within the sample chamber. In addition, the electroluminescent module is in optical communication with the sample chamber and is configured to emit light that facilitates a fluorescent chemical reaction sequence between the fluorophore-containing photometric enzymatic reagent and the analyte. Further details of such analytical test strips are described below and, in particular, with respect to FIGS. 1, 2, 3 and 4.

An analytical test strip for the determination of an analyte (such as glucose) in a bodily fluid sample (for example, a whole blood sample) according to other embodiments of the present invention include a substrate layer, an electroluminescent lamp disposed on the substrate layer, a sample chamber configured for receiving the bodily fluid sample disposed above the substrate layer; and an enzymatic reagent disposed within the sample chamber. Moreover, the electroluminescent lamp is configured to emit light, the light being visible to a user of the analytical test strip and providing the user with spatial awareness of the analytical test strip. Further details of such analytical test strips are described below and, in particular, with respect to FIGS. 1, 7, 8 and 9.

Figure 1:
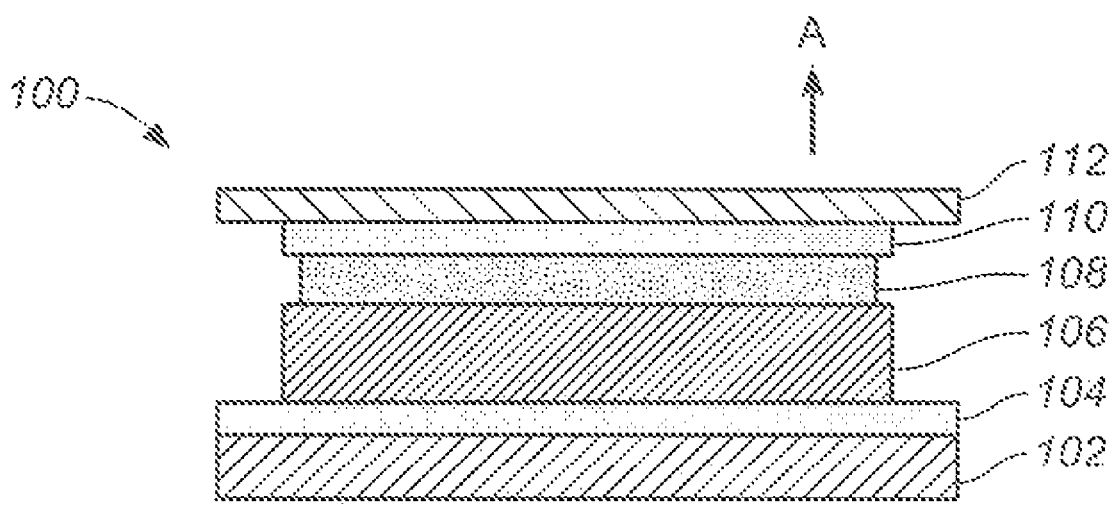
FIG. 1 is a simplified cross-sectional depiction of an electroluminescent component as can be included in analytical test strips according to embodiments of the present invention.

FIG. 1 is a simplified cross-sectional depiction of an electroluminescent component 100 as can be included in analytical test strips according to embodiments of the present invention. Electroluminescent component 100 can serve as either an electroluminescent module (as described with respect to, for example, FIGS. 2, 3 and 4) or as an electroluminescent lamp (as described with respect to, for example, FIGS. 7, 8 and 9). However, for the sake of simplicity, electroluminescent component 100 will be referred to as an electroluminescent module hereafter.

Electroluminescent module 100 includes a substrate layer 102, a rear electrode layer 104, an electrically-insulating layer 106 disposed over the rear electrode layer, a phosphor layer 108 disposed over electrically-insulating layer 106, and a front electrode layer 110, at least a portion of which is translucent to light emitted by phosphor layer 108, disposed over phosphor layer 108. Electroluminescent module 100 also includes an encapsulant layer 112 disposed over front electrode layer 110.

Substrate layer 102 can be formed of any suitable substrate layer material including, for example, a polyester substrate layer material or a commercially available Melinex® ST328 (manufactured by DuPont Teijin Films) substrate layer material.

Rear electrode layer 104 can be formed of any suitable electrically conductive material including, for example, indium tin oxide (ITO) that has been sputtered onto substrate layer 102 or gold. Rear electrode layer 104 can also be formed of carbon ink, silver paste or an electrically conductive polymer. In addition, rear electrode layer 104 can be, if desired, of any suitable pattern and can also be, for example, formed using conventional techniques such as screen-printing, laser ablation and photolithography.

Electrically insulating layer 106 can be formed, for example, of polyester, acrylic, or epoxy-based ink materials. Electrically insulating layer 106 serves to prevent undesirable short circuits when an AC current is applied across electroluminescent module 100 to induce the emission of light from phosphor layer 108 and, subsequently, from electroluminescent module 100. The AC current can be applied, for example, when analytical test strips according to embodiments of the present invention are inserted into an associated analytical meter.

Phosphor layer 108 can be formed of any suitable phosphor material known to one skilled in the art as suitable for use in an electroluminescent module or electroluminescent lamp. Examples of such phosphor materials are described in U.S. Pat. No. 5,675,217, which is hereby incorporated in full by reference. Moreover, the phosphor can, for example, include zinc chloride micro-crystals.

Front electrode layer 110 can be formed, for example, of translucent Indium Tin Oxide (ITO) or translucent gold for example. Light emitted from electroluminescent module 100 will pass through the translucent portion of front electrode layer 110 in, for example, the direction of arrow A in FIG. 1.

Encapsulant layer 112 is configured to provide a moisture barrier and, thus, protect phosphor layer 108 from moisture-induced degradation while still providing for light to be emitted from electroluminescent module 100. Therefore, encapsulant layer 112 can be formed, for example, of any suitably transparent and moisture impermeable material. Suitable materials include epoxy resins, silicones and polyurethanes. Moreover, as described in more detail below, a wavelength modulator can be embedded or dispersed within encapsulate layer 112.

Figure 2:
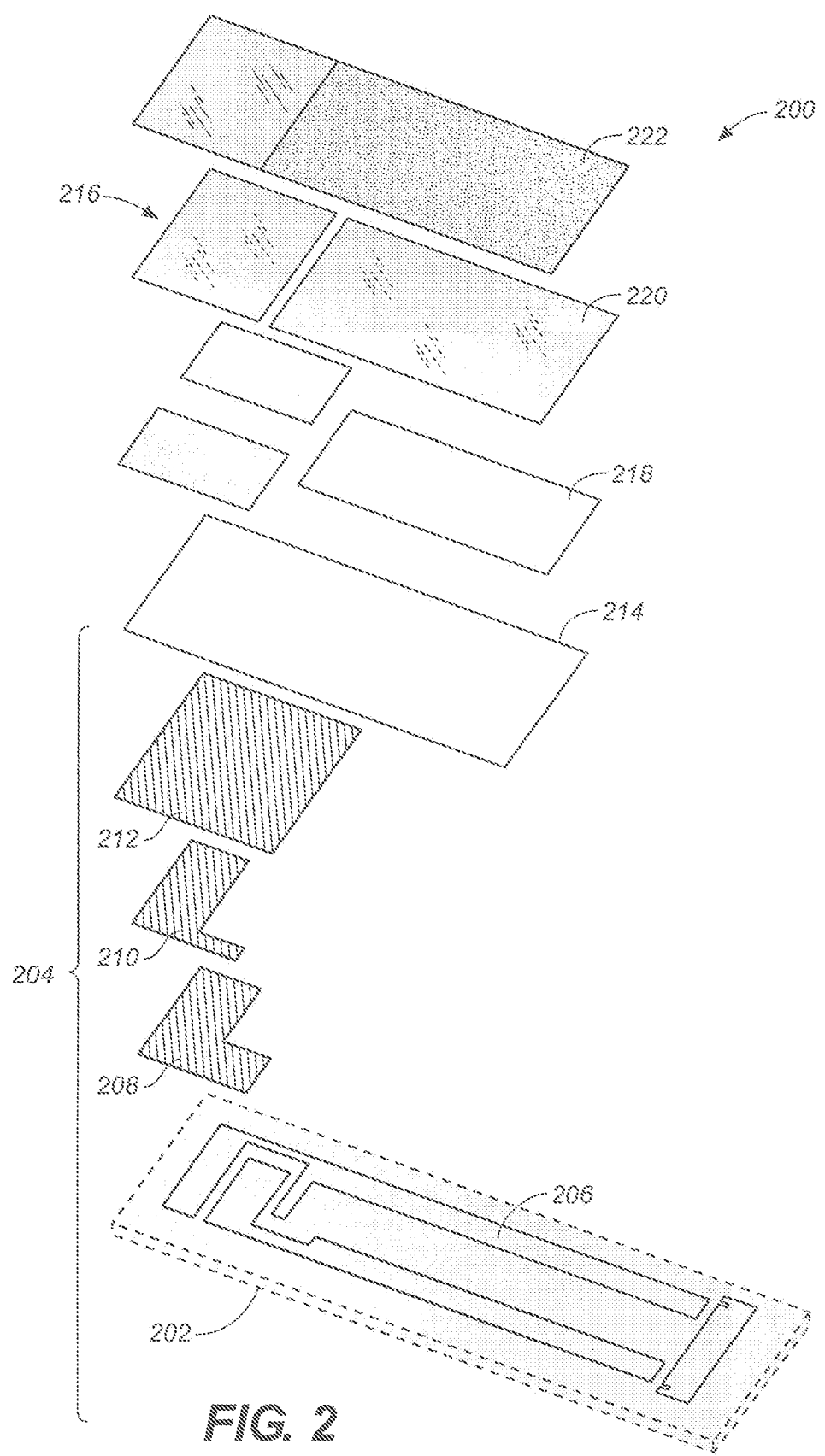
FIG. 2 is a perspective exploded view of an analytical test strip including an electroluminescent module according to an exemplary embodiment of the present invention.

FIG. 2 is a simplified perspective and exploded view of an analytical test strip 200 according to an embodiment of the present invention. Analytical test strip 200 includes a substrate layer 202 (depicted by dashed lines), an electroluminescent module 204 (including substrate layer 202 as well as a rear electrode layer 206, an electrically-insulating layer 208, a phosphor layer 210, a front electrode layer 212 and an encapsulant layer 214), and a sample chamber 216 (defined by adhesive layer 218, anti-fog layer 220, and top layer 222). In the embodiment of FIG. 2, sample chamber 216 is a capillary sample chamber.

Also included in analytical test strip 200 is a fluorophore-containing photometric enzymatic reagent (not shown in FIG. 2) disposed within sample chamber 216. Such a fluorophore-containing photometric enzymatic reagent could be, for example, disposed as a layer between encapsulant layer 214 and adhesive layer 218.

In general, fluorophore-containing photometric enzymatic reagents employed in embodiments of the present invention include (i) enzymes specific to a predetermined analyte and fluorescent chemical reaction sequence of interest, such as glucose oxidase and horseradish peroxidase (HRP) respectively and (ii) a fluorophore, such as, for example, Amplex Red reagent (i.e., 10-acetyl-3,7-duhydroxypehnoxazinne reagent), the proprietary and commercially available fluorophore DuoLux, coumarin, fluorescene isothio cynate (FITC), fluorescamine, and cascade blue.

It should be noted that the term "fluorophore" includes, but is not limited to, reagents such as Amplex Red reagent that are themselves non-fluorescent but that serve as fluorogenic probes by producing, for example, a fluorescent dye during a fluorescent chemical reaction sequence involving the fluorophore-containing photometric reagent, the analyte and light emitted from the electroluminescent module. Such fluorescent chemical reaction sequences are described further below with respect to FIGS. 3 and 4.

The fluorophore-containing photometric enzymatic reagents can also contain, for example, a suitable buffer (such as a citrate buffer, a phosphate buffer, or a citraconate buffer) and a binder (e.g., HEC (hydroxyethly cellulose), PVA (polyvinyl alcohol), polyaniline, or CMC (carboxymethylcellulose)). By means of comparison and background, typical components of conventional photometric enzymatic reagents are described in, for example, U.S. Pat. No. 5,453,360, which is hereby incorporated in full by reference.

As mentioned above, the enzyme included in the fluorophore-containing photometric enzymatic reagent is predetermined based on the analyte of interest. Therefore, other suitable enzymes include, but are nor limited to, cholesterol oxidase (for the analyte cholesterol) and amino-acid oxidase (for various amino acid analytes). In the embodiment of FIG. 2, fluorescent light emitted from phosphor layer 210 of electroluminescent module 204 propagates through front electrode layer 212 and encapsulant layer 214 to reach sample chamber 216. The fluorescent light then facilitates a fluorescent chemical reaction sequence involving the fluorophore-containing photometric enzymatic reagent and the analyte within sample chamber 216.

Figure 3:
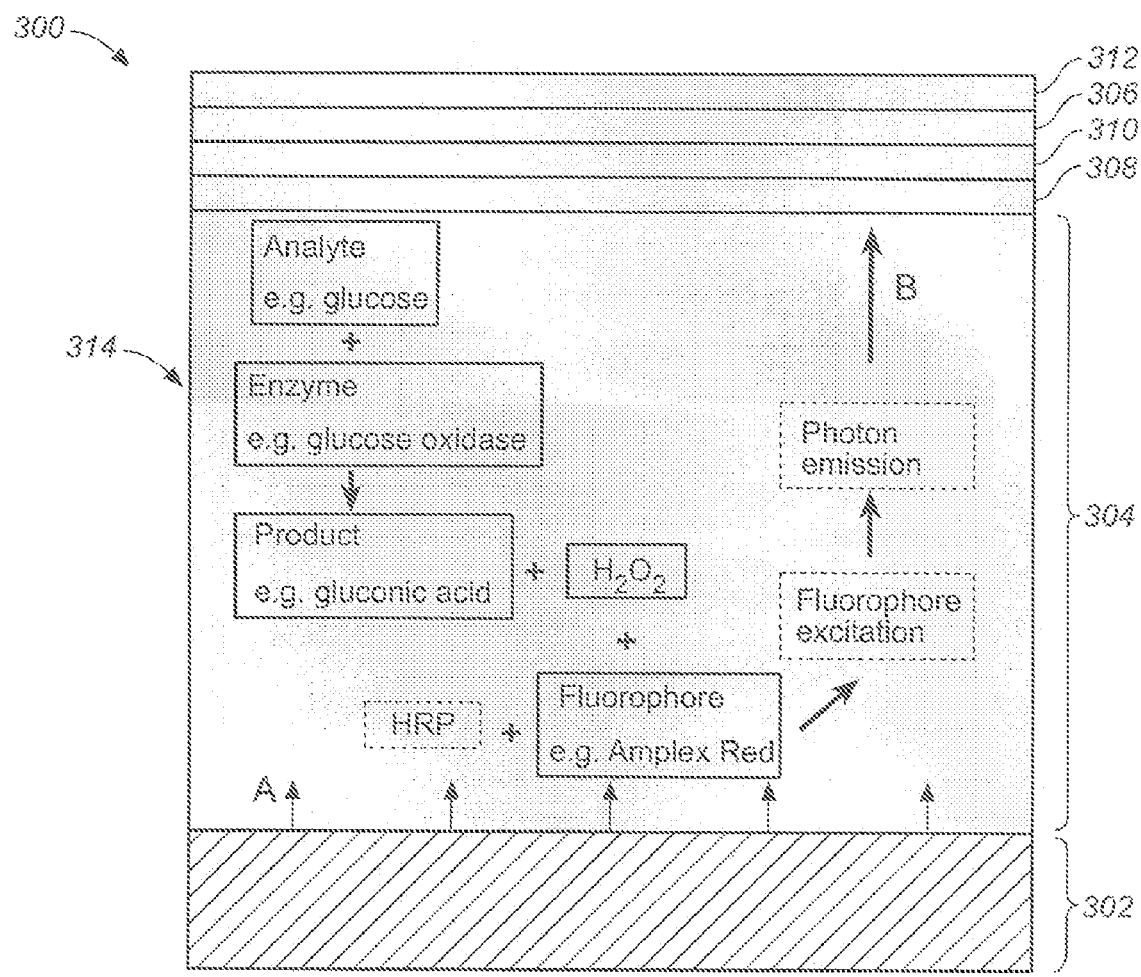
FIG. 3 is a simplified schematic diagram of a portion of an analytical test strip according to another embodiment of the present invention that includes a simplified depiction of a fluorescent chemical reaction sequence occurring within a sample chamber of the analytical test strip.

FIG. 3 is a simplified schematic diagram of a portion of an analytical test strip 300 according to another embodiment of the present invention that includes a simplified depiction of a fluorescent chemical reaction sequence occurring within a sample chamber of the analytical test strip. Portion 300 includes an electroluminescent module 302, a sample chamber 304, a photodetector 306, an adhesive layer 308, an anti-fog layer 310 and a top layer 312. Moreover, sample chamber 304 has a sample inlet 314 whereby a bodily fluid sample (e.g., a whole blood sample) is introduced into sample chamber 304.

A fluorescent chemical reaction sequence (as previously described) occurs within sample chamber 304. In the embodiment of FIG. 3, the fluorescent chemical reaction sequence includes the following reactions involving the bodily fluid sample (and analyte therein), the fluorophore-containing photometric enzymatic reagent and light from electroluminescent module 302 (depicted by the arrows labeled A in FIG. 3):

(1) an analyte (e.g., glucose)+enzyme (e.g., glucose oxidase) react to produce a product (e.g., gluconic acid) and $H_2O_2$;

(2) $H_2O_2$ (from (1) above) reacts with a fluorophore (e.g., Amplex Red reagent) and horseradish peroxidase (HRP), under the influence of light from electroluminescent module 302, to produce a fluorescent molecule (e.g., resorufin); and (3) the fluorescent molecule undergoes fluorophore excitation, resulting in photon emission (arrow B in FIG. 3)

In the embodiment of FIG. 3, the fluorescence of the fluorescent molecule (e.g., resorufin) results in the emission emits photons proportional to the concentration of analyte in the bodily fluid sample. These photons are then detected by photodetector 306, that is disposed in a co-facial arrangement with respect to electroluminescent module 302. Photodetector 306 can be formed, for example, from cadmium sulphide and cadmium selenide in the form of a resistive electrode.

Figure 4:
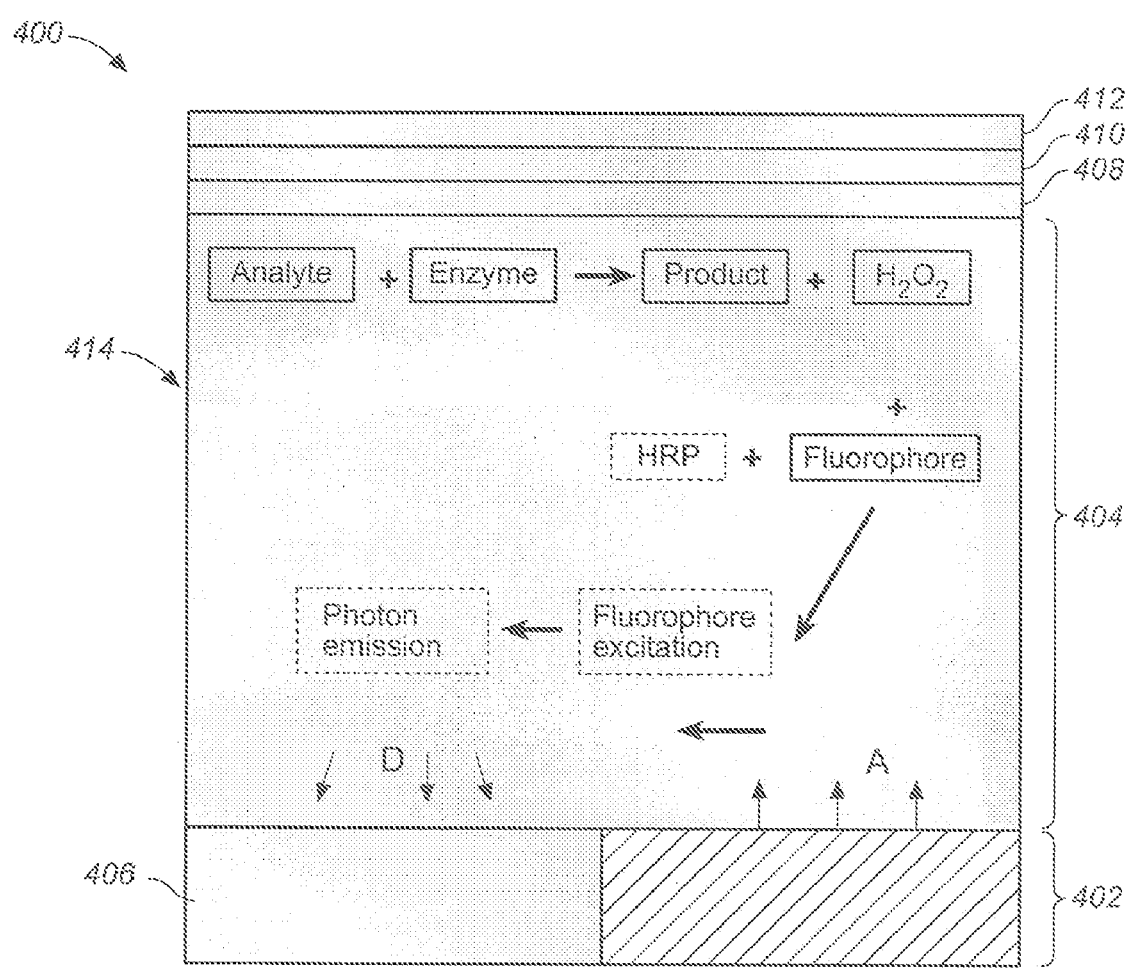
FIG. 4 is a simplified schematic diagram of a portion of an analytical test strip according to yet another exemplary embodiment of the present invention that includes a simplified depiction of a fluorescent chemical reaction sequence occurring within a sample chamber of the analytical test strip.

FIG. 4 is a simplified schematic diagram of a portion of an analytical test strip 400 according to yet another exemplary embodiment of the present invention that includes a simplified depiction of a fluorescent chemical reaction sequence occurring within a sample chamber of the analytical test strip. Portion 400 includes an electroluminescent module 402, a sample chamber 404, a photodetector 406, an adhesive layer 408, an anti-fog layer 410 and a top layer 412. Moreover, sample chamber 404 has a sample inlet 414 whereby a bodily fluid sample (e.g., a whole blood sample) is introduced into sample chamber 404.

A fluorescent chemical reaction sequence (as previously described) occurs within sample chamber 404. In the embodiment of FIG. 4, the fluorescent chemical reaction sequence includes the following general reactions involving the bodily fluid sample (and analyte therein), the fluorophore-containing photometric enzymatic reagent and light from electroluminescent module 402 (depicted by the arrows labeled A in FIG. 4):

(1) an analyte+an analyte-specific enzyme react to produce a product+$H_2O_2$;

(2) $H_2O_2$ (from (1) immediately above) reacts with a fluorophore and HRP, under the influence of light from electroluminescent module 402, to produce a fluorescent molecule (not shown in FIG. 4); and (3) the fluorescent molecule undergoes fluorophore excitation, resulting in photon emission (arrows D in FIG. 4)

In the embodiment of FIG. 4, the fluorescence of the fluorescent molecule results in the emission of photons proportional to the concentration of analyte in the bodily fluid sample. These photons are then detected by photodetector 406, which is disposed in a co-planar arrangement with respect to electroluminescent module 402. Such a co-planar arrangement can be beneficial in reducing interference with photodetector 406 by light from electroluminescent module 402. The photons reaching photodetector 406 are converted into a current. The current is translated into an analyte concentration by software within an associated analytical meter.

Once apprised of the present disclosure, one skilled in the art will recognize that light from electroluminescent modules in embodiments of the present invention serves to drive photochemistry of the fluorescent chemical reaction sequence. Such photochemically-driven fluorescent chemical reactions sequences are expected to provide highly precise and accurate analyte determinations via photon amplification (multiplication) behavior.

It should be noted that the absorbance maximum of Amplex Red reagent is at approximately 560 nm and its emission maximum is at approximately 590 nm. In certain embodiments of the present invention, a fluorescent product of Amplex Red reagent is resorufin, which has absorption and emission maxima that are sufficiently distinct from those of Amplex Red reagent such that there is expected to be little interference from auto-fluorescence for a majority of bodily fluid samples.

Electroluminescent modules and lamps employed in embodiments of the present invention would typically emit light in the blue-green wavelength region of the visible spectrum, at approximately 490 nm. However, for purposes of driving a fluorescent chemical reaction sequence, it can be advantageous to use excitation light in the orange-red wavelength region that is obtained by wavelength modulation of light emitted by a phosphor layer of an electroluminescent module. Such wavelength modulation is known, in general, as a Stoke's shift.

For example, since the absorbance maximum of Amplex Red reagent is approximately 560 nm, wavelength modulation can be used to provide light of an appropriate wavelength and intensity for use with fluorophore-containing photometric enzymatic reagents that include Amplex Red reagent. Such wavelength modulation can be achieved using, for example, fluorescein (with an absorption peak around 490 nm, and an emission spectrum with a maximum around 520 nm) or rhodamine with a maximum absorption around 530 nm, and a broad emission spectrum up to approximately 700 nm.

Wavelength modulators (such as fluorescein and rhodamine) can be incorporated into electroluminescent modules (and electroluminescent lamps) by, for example, dispersing or embedding the wavelength modulator into an encapsulant layer or by formation as an independent layer above or below an encapsulant layer.

Figure 5:
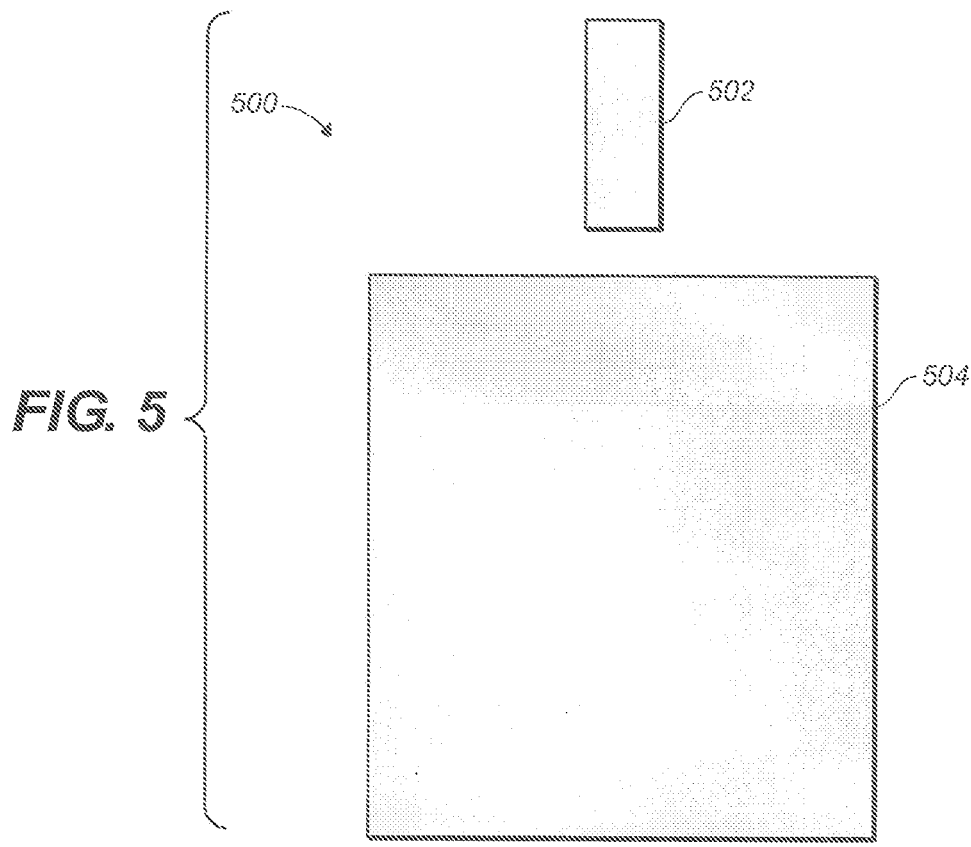
FIG. 5 is a simplified schematic depiction of a system for the determination of an analyte in a bodily fluid sample according to an exemplary embodiment of the present invention.

FIG. 5 is a simplified schematic depiction of a system 500 for the determination of an analyte in a bodily fluid sample according to an exemplary embodiment of the present invention. System 500 includes an analytical test strip 502 and an analytical meter 504.

Analytical test strip 502 can be any suitable analytical test strip according to embodiments of the present invention. Therefore, analytical test strip 502 has a substrate layer, an electroluminescent component (either an electroluminescent module and/or an electroluminescent lamp) disposed on the substrate layer, and a sample chamber configured for receiving a bodily fluid sample disposed above the substrate layer. Analytical meter 504 is configured for insertion of the analytical test strip therein and subsequent determination of the analyte as described elsewhere herein.

Figure 6:
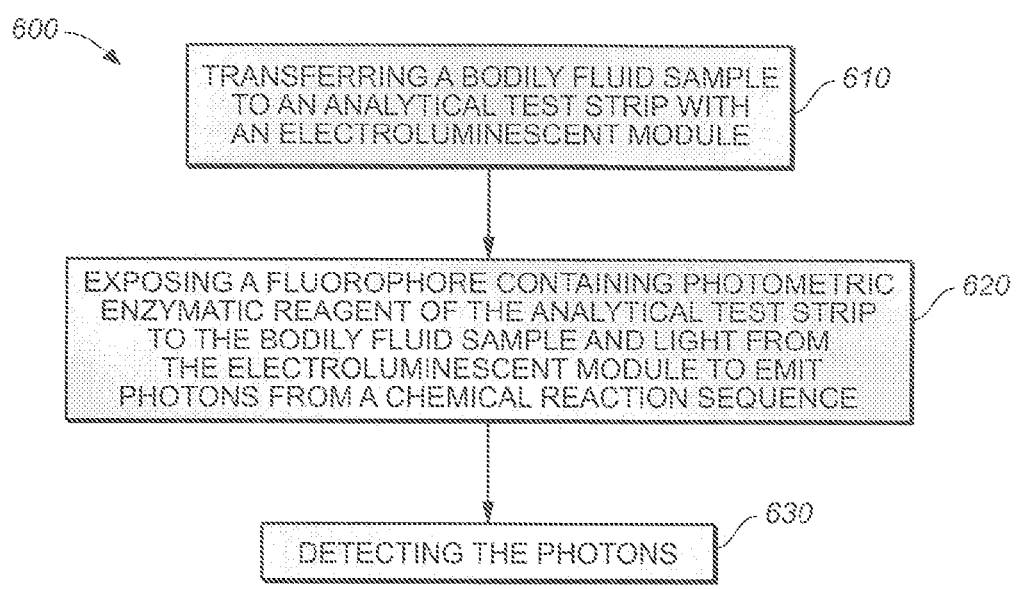
FIG. 6 is a flow diagram depicting stages in a process for determining an analyte in a bodily fluid sample according to an exemplary embodiment of the present invention.

FIG. 6 is a flow diagram depicting stages in a method 600 for determining an analyte (such as glucose) in a bodily fluid sample (for example a whole blood sample) according to an exemplary embodiment of the present invention. Method 600 includes transferring a bodily fluid sample to a sample chamber of an analytical test strip, as set forth in step 610.

The analytical test strip to which the bodily fluid sample is transferred includes a substrate layer, an electroluminescent module disposed on the substrate layer and in optical communication with the sample chamber, a fluorophore-containing photometric enzymatic reagent disposed within the sample chamber. Moreover, the electroluminescent module of the analytical test strip is configured to emit light that facilitates a fluorescent chemical reaction sequence involving the fluorophore-containing photometric enzymatic reagent and the analyte.

Method 600 also includes, at step 620, exposing the fluorophore-containing photometric enzymatic reagent to the bodily fluid sample and to light emitted from the electroluminescent module such that photons are emitted from the fluorophore-containing photometric enzymatic reagent via a fluorescent chemical reaction sequence. The photons are then detected with a photodetector, as set forth in step 630.

Once apprised of the present disclosure, one skilled in the art will recognize that methods for the determination of an analyte according to embodiments of the present invention can include steps that utilize any of the characteristics and features of analytical test strips and systems according to embodiments of the present invention.

Figure 7:
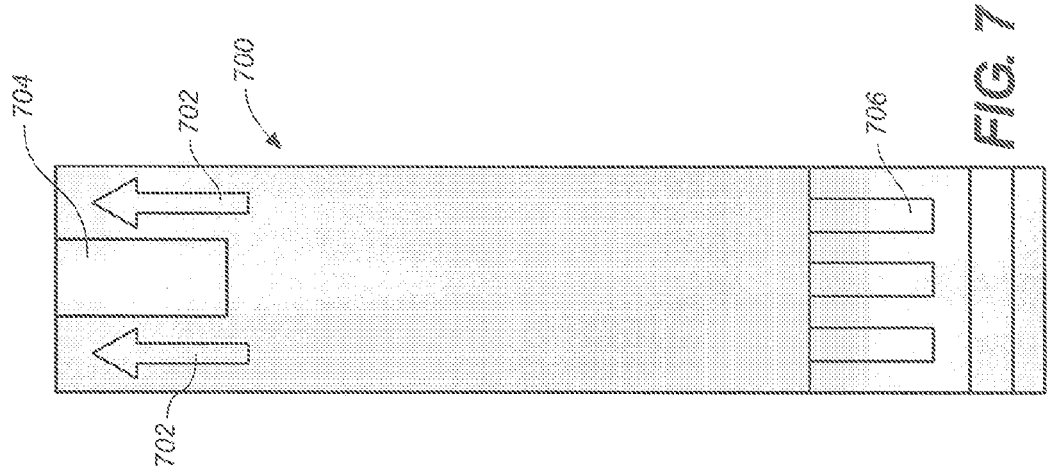
FIG. 7 is a simplified top view of an analytical test strip with an electroluminescent lamp according to an exemplary embodiment of the present invention.

FIG. 7 is a simplified top view of an analytical test strip 700 with an electroluminescent lamp according to an exemplary embodiment of the present invention. Analytical test strip 700 includes a substrate layer (not shown), an electroluminescent lamp 702 disposed on the substrate layer, a sample chamber 704 configured for receiving the bodily fluid sample disposed above the substrate layer and an enzymatic reagent (not depicted) disposed within the sample chamber. Analytical test strip 700 also includes electrical contacts 706 for conducting power and signals to and from various components of the analytical test strip.

Electroluminescent lamp 702 is configured to emit light, the light being visible to a user of the analytical test strip and providing the user with spatial awareness of the analytical test strip. In particular, in the embodiment of FIG. 7, electroluminescent lamp 702 is configured to emit light that appears as two directional arrows to a user, with the directional arrows indicating a bodily fluid sample application area of the analytical test strip.

Figure 8:
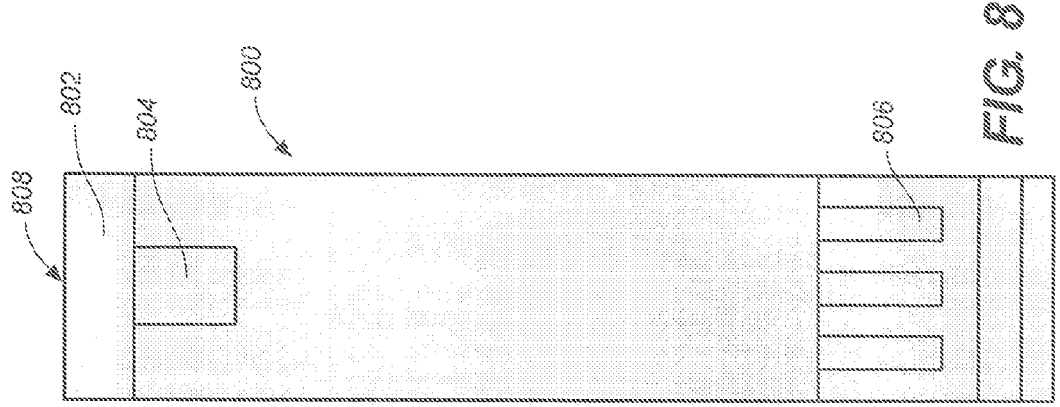
FIG. 8 is a simplified top view of an analytical test strip with an electroluminescent lamp according to another exemplary embodiment of the present invention.

FIG. 8 is a simplified top view of an analytical test strip 800 with an electroluminescent lamp according to another exemplary embodiment of the present invention. Analytical test strip 800 includes a substrate layer (not shown), an electroluminescent lamp 802 disposed on the substrate layer, a sample chamber 804 configured for receiving the bodily fluid sample disposed above the substrate layer and an enzymatic reagent (not depicted) disposed within the sample chamber. Analytical test strip 800 also includes electrical contacts 806 for conducting power and signals to and from various components of the analytical test strip.

Electroluminescent lamp 802 is configured to emit light, the light being visible to a user of the analytical test strip and providing the user with spatial awareness of the analytical test strip. In particular, in the embodiment of FIG. 8, electroluminescent lamp 802 is configured to emit light in a continuous band along a distal end 808 of the analytical test strip where the bodily fluid sample is to be applied.

Figure 9:
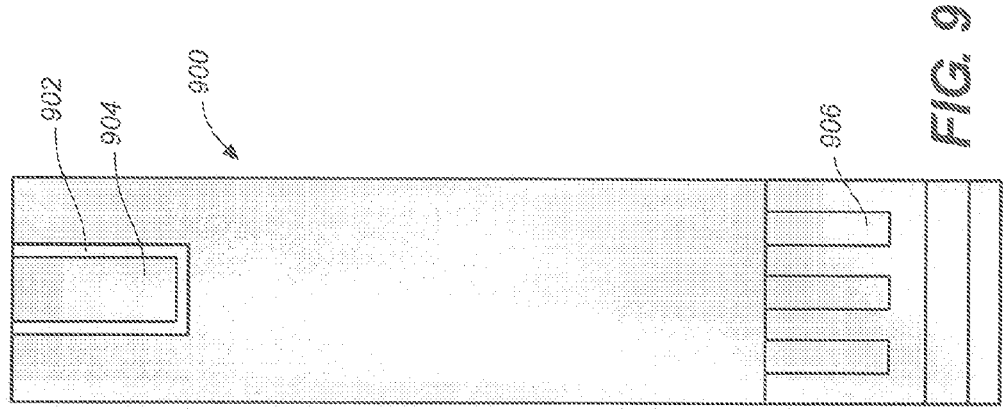
FIG. 9 is a simplified top view of an analytical test strip with an electroluminescent lamp according to yet another exemplary embodiment of the present invention.

FIG. 9 is a simplified top view of an analytical test strip 900 with an electroluminescent lamp according to yet another exemplary embodiment of the present invention. Analytical test strip 900 includes a substrate layer (not shown), an electroluminescent lamp 902 disposed on the substrate layer, a sample chamber 904 configured for receiving the bodily fluid sample disposed above the substrate layer and an enzymatic reagent (not depicted) disposed within the sample chamber. Analytical test strip 900 also includes electrical contacts 906 for conducting power and signals to and from various components of the analytical test strip.

Electroluminescent lamp 902 is configured to emit light, the light being visible to a user of the analytical test strip and providing the user with spatial awareness of the analytical test strip. In particular, in the embodiment of FIG. 9, electroluminescent lamp 902 is configured to emit light along a periphery of the sample chamber (for example, a capillary sample chamber) to facilitate visual determination of complete capillary sample fill by a bodily fluid sample.

Once apprised of the present disclosure, one skilled in the art will recognize that analytical test strips with electroluminescent lamps according to embodiments of the present invention can employ and suitable features and characteristics of analytical test strips with electroluminescent modules and systems according to embodiments of the present invention. Moreover, analytical test strips with electroluminescent lamps according to embodiments of the present invention can be electrochemical-based analytical test strips or photochemical-based analytical test strips.

Figure 10:
FIG. 10 is a flow diagram depicting stages in a process for manufacturing an analytical test strip for determination of an analyte in a bodily fluid sample according to an exemplary embodiment of the present invention.
Figure 11:
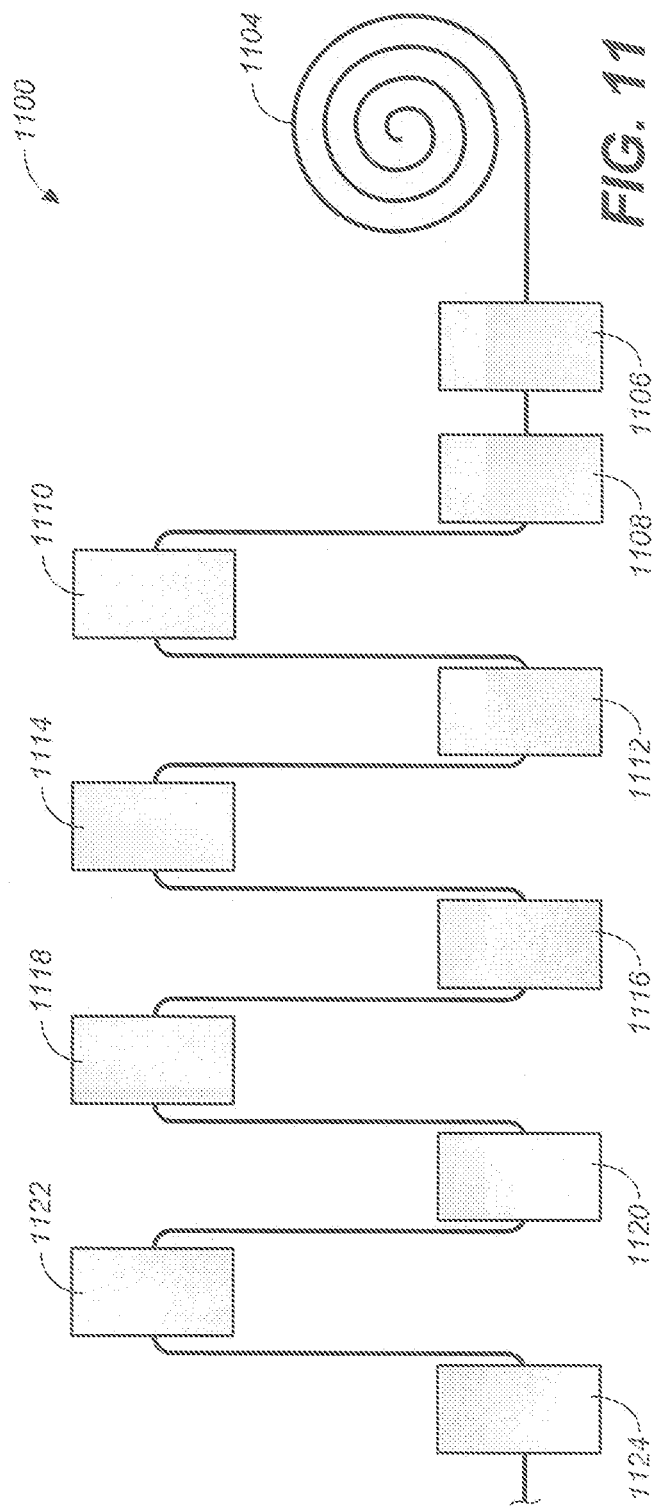
FIG. 11 is a simplified depiction of a continuous web printing apparatus as can be employed in embodiments of the present invention.

FIG. 10 is a flow diagram depicting stages in a method 1000 for manufacturing an analytical test strip for determination of an analyte (such as glucose) in a bodily fluid sample (for example a whole blood sample) according to an exemplary embodiment of the present invention. FIG. 11 is a simplified depiction of a continuous web printing apparatus 1100 as can be employed in method 1000 and other method embodiments of the present invention.

Referring to FIG. 10, method 1000 includes at step 1010, sequentially applying to a substrate layer, a:
(i) rear electrode layer,
(ii) an electrically-insulating layer disposed over the rear electrode layer,
(iii) a phosphor layer disposed over the electrically insulating layer, and
(iv) a front electrode layer, at least a portion of which is translucent, disposed over the phosphor layer.

The sequential application is accomplished such that it forms an electroluminescent component (either an electroluminescent lamp or an electroluminescent module as described herein with respect to various embodiments of the present invention) of the analytical test strip. If desired, any of the sequential applications can be followed by a drying step prior to the next sequential application (i.e., an intermittent drying step). Moreover, an encapsulant layer can also be sequentially applied.

Method 1000 can be accomplished using screen-printing technology, flat-bed printing, continuous web-based printing technology or any combination thereof. In this respect, continuous web-based printing technology can be especially beneficial in terms of printing yield and alignment. For example, continuous web printing apparatus 1100 can be employed with a substrate 1104 to conduct method 1000. In this circumstance, an optional preconditioning station 1106, a rear electrode layer print station 1108, a first dryer 1110, an electrically-insulating layer print station 1112, a second dryer 1114, a phosphor layer print station 1116, a third dryer 1118, a translucent front electrode layer print station 1120, a fourth dryer 1122 and an encapsulant layer print station 1124 can be employed to manufacture analytical tests strips.

Once apprised of the present disclosure, one skilled in the art will recognize that methods for manufacturing analytical test strips according to the present invention can be used to manufacture analytical test strips according to the present invention including, but not limited to, analytical test strips as depicted in FIGS. 2, 3, 4, 7, 8 and 9.

It should be understood that various alternatives to the embodiments of the invention described herein may be employed in practicing the invention. It is intended that the following claims define the scope of the invention and that structures and methods within the scope of these claims and their equivalents be covered thereby.

The invention claimed is:
1. A system for the determination of an analyte in a bodily fluid sample, the system comprising:
an analytical test strip that includes:
a substrate layer;

an electroluminescent component disposed on the substrate layer, the electroluminescent component including:
- a rear electrode layer;
- an electrically-insulating layer disposed over the rear electrode layer;
- a phosphor layer disposed over the electrically insulating layer:
- a front electrode layer, at least a portion of which is translucent, disposed over the phosphor layer; and
- an encapsulant layer: and
- a sample chamber configured for receiving a bodily fluid sample disposed above the substrate layer; and
- an analytical meter configured for insertion of the analytical test strip therein and subsequent determination of an analyte in the bodily fluid sample.

2. The system of claim 1 wherein the electroluminescent component is an electroluminescent module and wherein the analytical test strip also includes a fluorophore-containing photometric enzymatic reagent disposed within the sample chamber, and a photodetector disposed above the substrate layer, wherein the electroluminescent module is in optical communication with the sample chamber, and wherein the electroluminescent module is configured to emit light that facilitates a fluorescent chemical reaction sequence between the fluorophore-containing photometric enzymatic reagent and the analyte.

3. The system of claim 2 wherein the photodetector includes a photo-resistor electrode formed from one of cadmium sulphide and cadmium selenide.

4. The system of claim 2 wherein the fluorophore-containing photometric enzymatic reagent includes glucose oxidase, horseradish peroxidase, Amplex Red reagent and any combinations thereof.

5. The system of claim 2 wherein the fluorescent chemical reaction sequence produces resorufin such that fluorescence of the resorufin emits photons proportional to the concentration of analyte in the bodily fluid sample.

6. The system of claim 2 wherein the electroluminescent module is an electroluminescent lamp, and
wherein the electroluminescent lamp is configured to emit light, the light being visible to a user of the analytical test strip and providing the user with spatial awareness of the analytical test strip.

7. The system of claim 1 wherein the analytical test strip and analytical meter are configured for the determination of glucose in a whole blood sample.

8. The system of claim 1 wherein the electroluminescent component further includes a wavelength modulation layer configured to shift the wavelength of light emitted by the phosphor layer, the wavelength modulation layer embedded or dispersed within the encapsulant layer.

9. The system of claim 8 wherein the wavelength modulation layer includes fluorescein.

10. The system of claim 8 wherein the wavelength modulation layer includes rhodamine.

11. The system of claim 8 wherein the wavelength modulation layer shifts the wavelength of light emitted by the phosphor layer via a Stoke's shift.

* * * * *